United States Patent [19]

Dodge

[11] 4,210,245

[45] Jul. 1, 1980

[54] ADHESIVE PAD PACKAGE

[76] Inventor: George W. Dodge, 3902 Clay St., San Francisco, Calif. 94118

[21] Appl. No.: 19,875

[22] Filed: Mar. 12, 1979

[51] Int. Cl.² .................... B65D 73/00; B65D 85/62; A61F 5/30

[52] U.S. Cl. ................................. 206/440; 128/153; 206/460; 206/820

[58] Field of Search .............. 206/438, 440, 460, 813, 206/820; 128/153

[56] References Cited

U.S. PATENT DOCUMENTS

| 2,001,862 | 5/1935 | Battey | 128/153 |
| 3,063,555 | 11/1962 | Hanington | 206/440 |
| 3,467,250 | 9/1969 | D'Elia et al. | 206/820 |

*Primary Examiner*—William T. Dixson, Jr.
*Attorney, Agent, or Firm*—Gordon Wood

[57] ABSTRACT

A package of adhesive pads for use on corns, callouses and the like is provided in the form of a sheet of pad material such as moleskin and a relatively thin sheet of plastic adhered thereto. Both sheets are die cut along a plurality of lines to form a plurality of pad elements. The lines of cut are interrupted to provide localized frangible connections between adjacent pad elements to permit the user to remove a selected element by breaking its connections to adjacent elements.

6 Claims, 3 Drawing Figures

U.S. Patent    Jul. 1, 1980    4,210,245
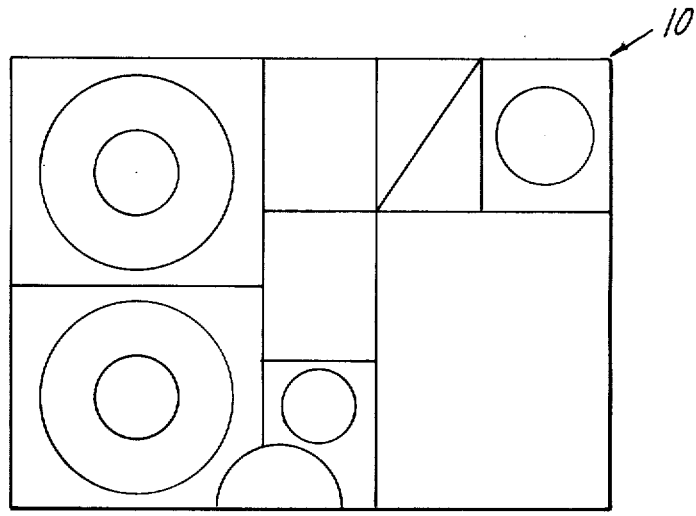
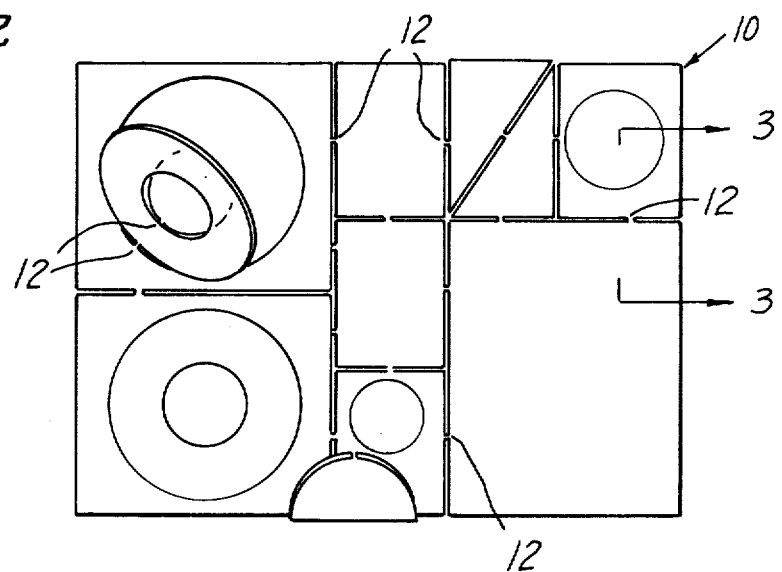
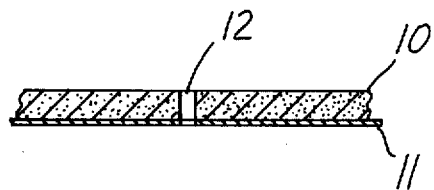

ADHESIVE PAD PACKAGE

This invention relates to the packaging of protective pads of the type used to protect afflicted portions of the body such as corns, callouses and the like.

Heretofore, it has been customary to merchandize protective pads in various different shapes to suit the particular part of the foot or other portion of the body which is to be protected. If such pad elements are sold in separated form in an envelope or like container it is difficult and time consuming to find and select the particular pad element desired. To overcome this problem some pads are sold in the form of sheets of moleskin or like material adhered by pressure sensitive adhesive to a thin backing sheet of plastic so that the particular shape desired may be cut with scissors from the two-layered sheet.

Another method of enhancing the convenience of using such pads is to adhere pad elements of various shapes to a backing sheet with the elements spaced apart so as to permit the user to remove the particular element desired. See, for example, U.S. Pat. Nos. 2,969,062 and 3,616,156.

The main object of the present invention is to overcome the disadvantages of prior art protective pad packages by providing a package which does not require the use of scissors and which does not require the retention of a backing sheet.

Another object of the invention is the provision of a protective pad package which facilitates the selection of the particular pad element desired and the removal thereof.

Yet another object of the invention is the provision of a protective pad package which is simple and inexpensive to manufacture and which lends itself to providing pad elements of numerous different shapes.

Still another object is the provision of a protective pad package which is convenient for the user to carry and which provides protection of the pressure sensitive adhesive surface at all times.

Other objects and advantages will be apparent from the following specification and drawings.

FIG. 1 is a plan view of the proferred form of the invention.

FIG. 2 is a view similar to FIG. 1 but with the various pad elements slightly separated or deflected out of the plane of the package to show the connecting portions between pad elements.

FIG. 3 is a greatly enlarged cross section taken in a plane indicated by lines 3—3 of FIG. 2.

In the particular form of the invention shown in FIGS. 1, 2 a rectangular sheet of moleskin 10 is adhered to a relatively thin backing sheet 11 of plastic or like material by means of pressure sensitive adhesive as is well known in the art.

The sheets are then die cut with the cutter knives cutting through both sheets to form the various different shaped pad elements shown. However, said cutter knives are arranged so that slight interruptions remain in the cuts to provide localized fragile connections between adjacent pad elements. Said connections, indicated at 12, need not be greater than 1/32" in width for the purpose of the present invention.

When the purchaser receives the package shown in FIG. 1 it will be apparent that it is a simple matter to remove the particular element desired by pulling on such element to break the localized frangible connection or connections attaching it to the remainder of the assembly.

I claim:

1. An adhesive pad package comprising:
   a pair of sheets,
   said pair including a planar sheet of pad material adhered to a relatively thin backing sheet of about the same area and extent,
   said sheets being both die cut along a plurality of lines to form a plurality of pad elements together composing the entire area of said sheets,
   the cuts along said lines being interrupted to provide at least one localized frangible connection between adjacent elements, whereby
   each element may be selectively removed from its adjacent elements by breaking its connection to said adjacent elements.

2. A package according to claim 1 wherein only one connection exists between one element and each of its adjacent elements.

3. A package according to claim 1 wherein the cuts along said lines form a plurality of different shaped pad elements.

4. A package according to claim 1 wherein said pad material is moleskin.

5. A package according to claim 1 wherein said connections are in the order of 1/32" wide.

6. A package according to claim 1 wherein said connections are less than 1/32" in width.

* * * * *